United States Patent [19]

Downs

[11] Patent Number: 4,823,418
[45] Date of Patent: Apr. 25, 1989

[54] BIRTH SAFETY NET

[76] Inventor: Margaret C. Downs, No. 1, 48th St., Valley, Ala. 36854

[21] Appl. No.: 214,593

[22] Filed: Jul. 1, 1988

[51] Int. Cl.⁴ .................... A47C 21/00; A47C 31/00; A61G 1/00
[52] U.S. Cl. ........................................ 5/503; 5/82 R; 5/98 B; 182/138
[58] Field of Search ................ 5/82 R, 89, 120, 98 B, 5/508, 482, 60, 503; 182/138, 139; 297/182, 192; 43/7, 14

[56] References Cited

U.S. PATENT DOCUMENTS

| | | | |
|---|---|---|---|
| 1,454,112 | 5/1923 | Graves | 5/89 |
| 4,723,327 | 2/1988 | Smith | 5/82 R |
| 4,742,587 | 5/1988 | Dove | 5/82 R |

FOREIGN PATENT DOCUMENTS

| | | | |
|---|---|---|---|
| 092784 | 2/1983 | European Pat. Off. | 5/109 |
| 636085 | 3/1928 | France | 5/90 |
| 15467 | of 1902 | United Kingdom | 182/138 |

Primary Examiner—Alexander Grosz
Attorney, Agent, or Firm—Michael C. Smith

[57] ABSTRACT

A birth safety net to prevent the dropping or falling of a new born child as it exits the birth canal comprising a fabric body, five sides, five corners and means for securring each corner to a portion of the birthing chair or birthing bed.

10 Claims, 1 Drawing Sheet

BIRTH SAFETY NET

TECHNICAL FIELD

The present invention relates generally to safety nets, and specifically to a birth safety net, and more specifically to a safety net for a new born child as it exits the birth canal.

BACKGROUND ART

Safety nets and similar devices are well known in the art. Examples are shown in U.S. Pat. No. 3,298,736; 2,938,574; 4,432,521; 2,827,953; 2,700,413; 2,607,052; 4,659,143; 4,094,547; and 1,377,860.

While the varieties of safety nets are apparently well suited for their particular uses, until the present invention there has been no birth safety net for use in providing a safety net for a new born child as it exits the birth canal to prevent the child from falling from the hands of delivery personnel to the floor. It is for this reason that the present birth safety net was invented.

DISCLOSURE OF INVENTION

The present invention promotes safe delivery of new born children. The present invention is a birth safety net having five corners, five sides, a generally open weave fabric, and retention means at each corner. It is particularly useful with birthing chairs and birthing beds.

Thus, a primary object of the present invention is to provide a safety net for new born children.

Another major object of this invention is to provide a five sided birth safety net for use with birthing chairs and birthing beds.

BRIEF DESCRIPTION OF THE DRAWINGS

While the specification concludes with claims particularly pointing out and distinctly claiming the subject matter which is regarded as the invention, it is believed that the invention, objects, features, and advantages thereof will be better understood from the following description taken in connection with the accompanied drawings in which like parts are given like identification numerals and wherein:

BEST MODE FOR CARRYING OUT THE INVENTION

Figure 1:
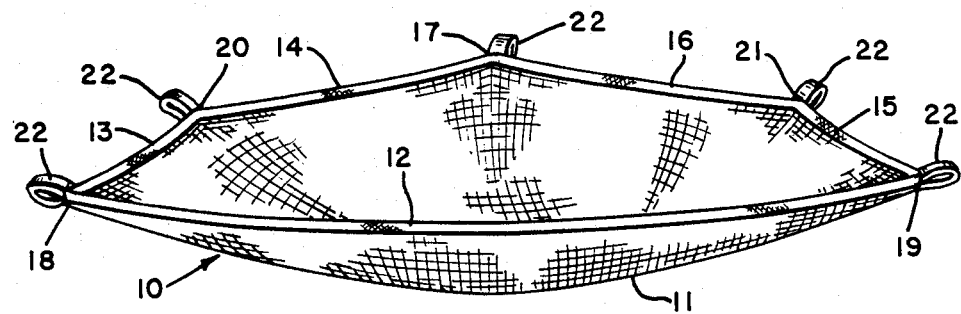
FIG. 1 is a perspective view of the present invention.

As FIG. 1 of the drawings illustrates, the preferred embodiment of the present birth safety net 10 comprises a substantially flat body 11 of open weave fabric, five sides 12, 13, 14, 15, 16, five corners 17, 18, 19, 20, 21, and attachment means 22 at each corner. Birth canal corner 17 is secured to the birthing chair or birthing bed (not shown) at a point immediately below the mother's birth canal by attachment means 22. Attachment means 22 are preferably the hook and loop type fastener, such as sold under the trademark "VELCRO", but may be other common means such as snaps or buckles. It is preferred that the hook and loop type attachment means have a series of hooks on the outer portion of a first member of the loop and a series of eyes on the inner portion of a second member of the loop which overlap for secure attachment. Directly opposite the birth canal corner 17, is the delivery personnel side 12 of the net 10, where the delivery person is generally located in anticipation of the appearance of the child. Left front corner 18 and right front corner 19 define the limits of delivery personnel side 12, and are each secured by attachment means 22 to portions of the delivery chair or bed in areas which are located approximately immediately below the left lower leg and right lower leg of the mother. Between the left front corner 18 and the birth canal corner 17 is a left rear corner 20 which is secured to the birthing chair or bed at a point approximately immediately below the right thigh of the mother by attachment means of 22. Left side 13 spans between left front corner 18 and left rear corner 20, and left birth side 14 spans between left rear corner 20 and birth canal corner 17. Between the right front corner 19 and the birth canal corner 17 is a right rear corner 21 which is secured to the birthing chair on bed by attachment means 22 at a point approximately immediately below the left thigh of the mother. Right side 15 spans between right front corner 19 and right rear corner 21, and right birth side 16 spans between right rear corner 21 and birth canal corner 17. The fabric of body 11 is sufficiently strong enough to support in excess of twenty pounds; sides 13, 14, 15, 16, are bound with a non-elastic material; and side 12 is bound with an elastic material to accomodate movement of delivery personnel and the child.

It is preferred that the inner angle of the birth canal corner 17 is about 160 angular degrees, the inner angle of right front corner 19 is about 85 angular degrees, the inner angle of left front corner 18 is about 85 angular degrees, the inner angle of left rear corner 20 is about 125 angular degrees, and the inner angle of right rear corner 21 is about 125 angular degrees. Left side 13 is about 18 inches long, right side 15 is about 18 inches long, left birth side 14 is about 11 inches long, and right birth side 16 is about 11 inches long. Delivery personnel side 12 is about 29 inches long and expands to about 38 inches in length.

There are occasions when a child quickly and unexpectedly exits the birth canal wtih sufficient time for delivery personnel to react to receive the child. With the use of the present invention on such occasions, the body 11 prevents downward movement of the child while the delivery pesonnel side 12 prevents forward movement of the child, and sides 13, 15 prevent lateral movement of the child, and the left rear and right rear sides 14, 16 in cooperation with the birth canal corner 17 prevent rearward movement of the child.

And added use for the net 10 is for the collection of blood and other fluids during and after the delivery . It prevents these fluids from unnecessarily splattering on delivery personnel and equipment and from unnecessarily spilling to the floor, thereby reducing the possibility of transmission of diseases.

Figure 2:
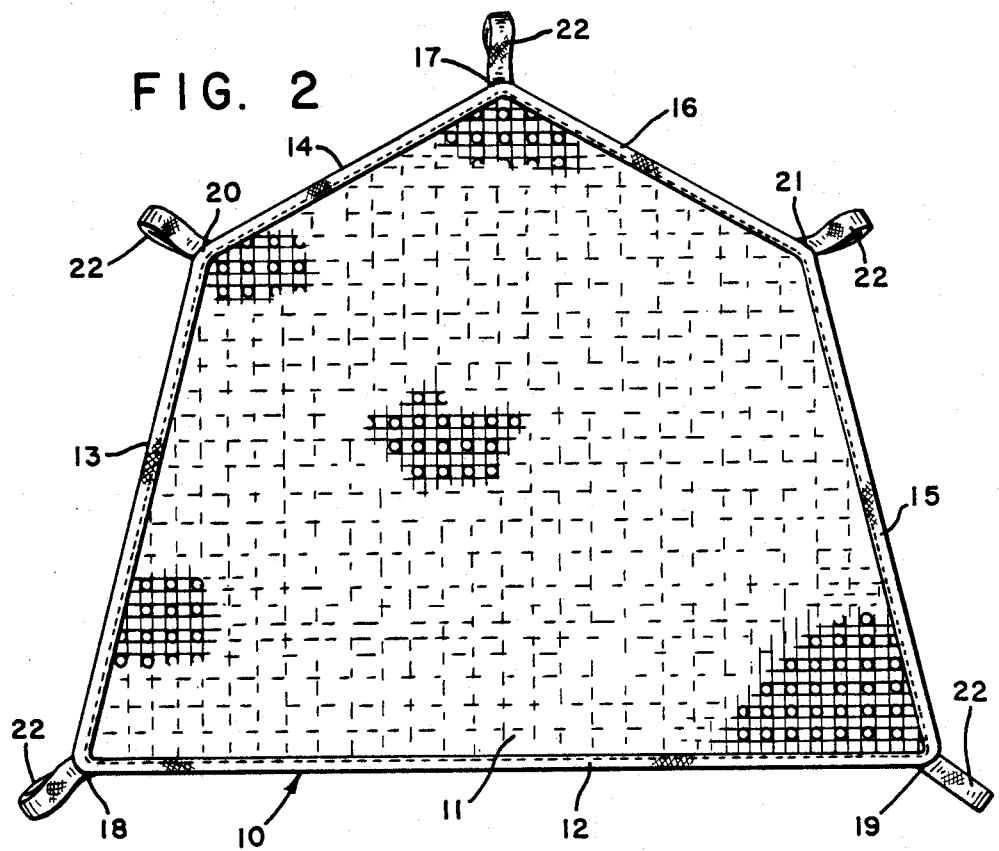
FIG. 2 is a top view of the present invention.

FIG. 2 shows the top of the net 10 which is substantially identical to the bottom of the net 10.

While this invention has been described in detail with particular reference to a preferred embodiment thereof, it will be understood that variations and modifications can be effective within the spirit and scope of the invention as described hereinbefore and as defined in the appended claims.

INDUSTRIAL APPLICABILITY

This invention is capable of exploitation in the hospital industry and is particularly useful in a system for providing for safe delivery of children.

I claim:

1. A birth safety net for use with a birthing chair or a birthing bed comprising:
   (a) a body of substantially flat fabric having five sides and five corners; and
   (b) attachment means at each corner for securring said safety net in five separate directions to said birthing chair or said birthing bed.

2. The apparatus of claim 1 wherein said body comprises an open weave fabric.

3. The apparatus of claim 2 wherein said attachment means comprises hook and loop type loops having a first loop member with a series of loops on its outer surface and a second loop member with a series of eyes on its inner surface, further provided that said surfaces overlap and contact to form said loop.

4. A birth safety net for use with a birthing chair or a birthing bed comprising:
   (a) a body for substantially flat fabric having five sides and five corners; and
   (b) attachment means at each corner for securing said safety net to said birthing chair or said birthing bed; further provided that
   said sides and and corners comprise a birth canal corner securable to the birthing chair or birthing bed at a point, when in use, immediately below the mother's birth canal; a delivery personnel side, directly opposite said birth canal corner; a left front corner at the left end of said delivery personnel side; a right front corner at the right end of said delivery personnel side; a left rear corner located, when in use, at a point below the right thigh of a mother using said birthing chair or birthing bed; a right rear corner located, when in use, at a point below the left thigh of a mother using said birthing chair or birthing bed; a left side spanning between said left front corner and said left rear corner; a right side spanning between said right front corner and said right rear corner; a left birth side spanning between said left rear corner and said birth canal corner; and a right birth side spanning between said right rear corner and said birth canal corner.

5. The apparatus of claim 4 wherein said fabric and said attachment means are sufficiently strong enough to support at least twenty pounds.

6. The apparatus of claim 5 wherein said left side, said right side, said left birth side and said right birth side are bound with non-elastic material.

7. The apparatus of claim 6 wherein said delivery personnel side is bound with elastic material.

8. The apparatus of claim 7 wherein the inner angle formed at said birth canal corner is about 160 angular degrees, the inner angle formed at said right front corner is about 85 angular degrees, the inner angle formed at said left front corner is about 85 angular degrees, the inner angle formed at said left rear corner is about 125 angular degrees, and the inner angle formed at said right rear corner is about 125 angular degrees.

9. The apparatus of claim 8 wherein said delivery personnel side is about 29 inches in length, said left side is about 18 inches in length, said right side is about 18 inches in length, said left birth side is about 11 inches in length, and said right birth side is about 11 inches in length.

10. The apparatus of claim 9 wherein said delivery personnel side is expandable to about 38 inches in length.

* * * * *